United States Patent [19]

Ferrini

[11] 4,309,353
[45] Jan. 5, 1982

[54] BENZOPYRANE DERIVATIVES

[75] Inventor: Pier G. Ferrini, Binningen, Switzerland

[73] Assignee: Ciba-Geigy Corporation, Ardsley, N.Y.

[21] Appl. No.: 97,025

[22] Filed: Nov. 21, 1979

Related U.S. Application Data

[62] Division of Ser. No. 826,224, Aug. 19, 1977, Pat. No. 4,205,082.

[30] Foreign Application Priority Data

Aug. 31, 1976 [LU] Luxembourg ............................ 75688

[51] Int. Cl.³ ............................................. C07D 311/08
[52] U.S. Cl. ............................ 260/343.45; 260/343.21; 546/256; 546/269
[58] Field of Search ................... 260/343.45, 343.21; 546/256, 269

[56] References Cited

U.S. PATENT DOCUMENTS

| | | | |
|---|---|---|---|
| 2,610,152 | 9/1952 | Ackermann | 260/343.45 |
| 3,008,969 | 11/1961 | Pretka | 260/343.45 |
| 3,201,406 | 8/1965 | Moffett | 546/269 |
| 3,681,397 | 8/1972 | Knupfer et al. | 260/343.45 |
| 3,792,063 | 2/1974 | Cairns et al. | 260/345.2 |
| 3,937,719 | 2/1976 | Sellstedt et al. | 260/345.2 |
| 3,947,462 | 3/1976 | Arendsen et al. | 546/269 |

Primary Examiner—Henry R. Jiles
Assistant Examiner—Jane T. Fan
Attorney, Agent, or Firm—Prabodh I. Almaula

[57] ABSTRACT

New benzopyrane derivatives of the general formula

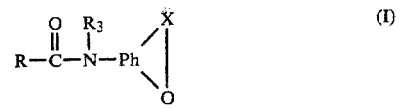

in which R is free, esterified or amidated carboxyl, Ph is 1,2-phenylene which contains the group R—CO—$NR_3$— and is otherwise unsubstituted or is substituted, X is a group of the formula —CO—$CR_1$=$CR_2$—, in which $R_1$ and $R_2$ independently of one another are hydrogen, acyl or a substituted or unsubstituted hydrocarbon radical or a hetero-analogue thereof, or conjointly are 3-membered to 5-membered lower alkylene, and $R_2$ can also be free or etherified hydroxyl or hydroxyl etherified by an organic carboxylic acid, and $R_3$ is hydrogen or lower alkyl, are useful as anti-allergic agents.

4 Claims, No Drawings

BENZOPYRANE DERIVATIVES

This is a divisional of application Ser. No. 826,224, filed on Aug. 19, 1977, now U.S. Pat. No. 4,205,082, issued May 27, 1980.

The invention relates to a process for the preparation of novel benzopyrane derivatives of the general formula

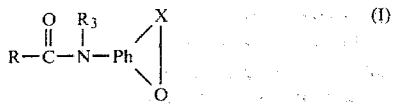

in which R is free, esterified or amidated carboxyl, Ph is 1,2-phenylene which contains the group $R-CO-NR_3-$ and is otherwise unsubstituted or is substituted, X is a group of the formula $-CO-CR_1=CR_2-$, in which $R_1$ and $R_2$ independently of one another are hydrogen, acyl or a substituted or unsubstituted hydrocarbon radical or a hetero-analogue thereof, or conjointly are 3-membered to 5-membered lower alkylene, and $R_2$ can also be free or etherified hydroxyl or hydroxyl etherified by an organic carboxylic acid, and $R_3$ is hydrogen or lower alkyl, in the free form or in the form of a salt, the novel compounds themselves, pharmaceutical formulations containing these compounds and the use of such formulations.

Esterified carboxyl is, for example, carboxyl esterified by a substituted or unsubstituted alcohol of aliphatic or aromatic character.

An alcohol of aliphatic character is an alcohol in which the C atom bonded to the hydroxyl group is not a member of an aromatic system, for example an aliphatic alcohol which is unsubstituted or substituted by substituted or unsubstituted aryl or hetero-aryl, for example substituted or unsubstituted phenyl or pyridyl, a possible alcohol of this type being, for example, a lower alkanol, or is a cycloaliphatic alcohol, for example a 5-membered to 8-membered cycloalkanol. Examples which may be mentioned of carboxyl esterified by a substituted or unsubstituted alcohol of aliphatic character are: lower alkoxy-carbonyl, for example methoxy-, ethoxy-, propoxy-, isopropoxy- and butoxy-carbonyl, phenyl-lower alkoxy-carbonyl, in particular α- and β-phenyl-lower alkoxy-carbonyl, which is unsubstituted or substituted in the phenyl part, possible substituted or unsubstituted phenyl and possible lower alkoxy being, in particular, those mentioned below, for example benzyloxycarbonyl and α- and β-phenethoxycarbonyl, and 5-membered to 8-membered cycloalkoxycarbonyl, for example cyclopentyloxy-, cyclohexyloxy- and cycloheptyloxy-carbonyl.

An alcohol of aromatic character is an alcohol in which the C atom bonded to the hydroxyl group is a member of a carbocyclic or heterocyclic aromatic system, for example a phenol which is unsubstituted or substituted in the phenyl part or a hydroxypyridine which is substituted by lower alkyl, such as methyl, or lower alkoxy, such as methoxy. Examples which may be mentioned of carboxyl esterified by a substituted or unsubstituted alcohol of aromatic character are: phenoxy-, tolyloxy-, anisyloxy- and chlorophenoxy-carbonyl and also 2-, 3- and 4-pyridyloxycarbonyl.

Amidated carboxyl contains, as the amino group, for example a free amino group or an amino group which is substituted by at least one substituted or unsubstituted hydrocarbon radical of aliphatic character, or a hetero-analogue thereof, or a substituted or unsubstituted aryl radical.

In a substituted or unsubstituted hydrocarbon radical of aliphatic character, or a hetero-analogue thereof, the free valency emanates from a non-aromatic C atom. A radical of this type is, for example, lower alkyl or lower alkenyl, which can be substituted by substituted or unsubstituted phenyl or naphthyl, or, for example, 5-membered to 8-membered cycloalkyl, such as cyclohexyl, or unsubstituted or lower alkylated, for example methylated, 4-membered to 7-membered alkylene, or a monooxa-, -aza- or -thia-analogue thereof, for example tetramethylene or pentamethylene or 3-oxa-, 3-aza- or 3-thia-pentamethylene. Examples which may be mentioned of carbamyl substituted by at least one such radical are: mono- or di-lower alkyl-carbamyl, such as N-methyl- and N,N-diethyl-carbamyl, phenyl-lower alkyl-carbamyl which in the phenyl part is unsubstituted or substituted as indicated below, such as N-benzyl- or N-(1- or 2-phenethyl)-carbamyl, or pyrrolidinocarbonyl, piperidinocarbonyl, morpholinocarbonyl, thiomorphininocarbonyl, piperazinocarbonyl or 4-lower alkyl-piperizinocarbonyl, for example 4-methyl-piperazinocarbonyl.

A substituted or unsubstituted aryl radical is, for example, substituted or unsubstituted naphthyl, or phenyl which is unsubstituted or substituted as indicated below and/or substituted on two adjacent ring atoms by a group $-OX-$, which has the meaning defined. Examples which may be mentioned of carbamyl groups substituted by a radical of this type are, for example, N-phenyl-, N-tolyl-, N-anisyl-, N-chlorophenyl- and N-naphthyl-carbamyl as well as groups of the formula

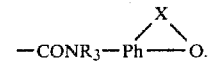

1,2-Phenylene Ph which contains the group $R-CO-NR_3-$ can also contain, in addition to this group, at least one, for example one or two, further substituents, examples of possible substituents being lower alkyl, such as those mentioned below, for example methyl, lower alkoxy, such as those mentioned below, for example methoxy, halogens, such as those mentioned below, for example chlorine, and trifluoromethyl.

Acyl is, for example, acyl derived from an organic carboxylic acid or from free, partially esterified or amidated carbonic acid.

Acyl derived from a carboxylic acid is, for example, lower alkanoyl or substituted or unsubstituted benzoyl, for example, acetyl, propionyl, butyryl or benzoyl.

Acyl derived from free, partially esterified or amidated carbonic acid is, for example, free, esterified or amidated carboxyl, such as free carboxyl or carboxyl esterified or amidated as indicated above, for example carboxyl, methoxy- or ethoxy-carbonyl or carbamyl.

Free or etherified hydroxyl is, for example, free hydroxyl or hydroxyl etherified by a lower alkanol or by a substituted or unsubstituted phenol, i.e. hydroxyl, lower alkoxy or substituted or unsubstituted phenoxy, for example hydroxyl, methoxy, ethoxy or phenoxy.

Free hydroxyl or hydroxyl esterified by carboxylic acid is, for example, free hydroxyl or hydroxy esterified by a lower alkanecarboxylic acid or by a substituted or unsubstituted benzoic acid, i.e. hydroxyl, lower alkanoyloxy or substituted or unsubstituted benzoyloxy, especially acetoxy, propionyloxy or benzoyloxy.

A substituted or unsubstituted hydrocarbon radical or a hetero-analogue thereof is, for example, a substituted or unsubstituted hydrocarbon radical of aliphatic character or a substituted or unsubstituted aromatic hydrocarbon radical or a hetero-analogue thereof.

3-membered to 5-membered lower alkylene can be straight-chain or branched and is, for example, 1,3-propylene, 1,4-butylene, 1,5-pentylene or 2- or 3-methyl-1,4-butylene.

In a substituted or unsubstituted hydrocarbon radical of aliphatic character the free valency emanates from a nonaromatic C atom. A radical of this type is, for example, an aliphatic hydrocarbon radical which is unsubstituted or substituted by substituted or unsubstituted phenyl, for example a lower alkyl radical, or a cycloaliphatic hydrocarbon radical, such as adamantyl or monocyclic 5-membered to 8-membered cycloalkyl or cycloalkenyl, for example 1-cycloalkenyl. Examples of such radicals which may be mentioned in particular are: methyl, ethyl, isopropyl and butyls, benzyl and methyl-, methoxy- and chloro-benzyls, cyclopentyl, cyclohexyl, 1-cyclohexenyl, cycloheptyl and 1-cycloheptenyl.

A substituted or unsubstituted aromatic hydrocarbon radical or a hetero-analogue thereof contains, for example 5 or 6 ring members and up to 2 hetero-atoms, such as a nitrogen, oxygen or sulphur atom, and is, for example, substituted or unsubstituted phenyl, such as one of those below, or a 5-membered or 6-membered heteroaryl radical containing a nitrogen, oxygen or sulphur atom, such as, for example, one of those below. Examples are, in particular, phenyl or pyridyl which are unsubstituted or substituted by methyl, methoxy or chlorine.

The following applies in the preceding and following text:

Substituted or unsubstituted phenyl and naphthyl and also phenyl in substituted or unsubstituted benzoyl, benzoyloxy and aromatic alcohols is, for example, phenyl or naphthyl which is unsubstituted or monosubstituted or polysubstituted, for example monosubstituted or disubstituted, possible substituents being, in particular, lower alkyl, lower alkoxy or halogens, for example those mentioned below, hydroxyl and also trifluoromethyl, such as phenyl, naphthyl, o-, m- or p-tolyl, o-, m- or p-anisyl, o- or p-chlorophenyl or 2,4-, 3,5- or 2,6-dichlorophenyl.

Substituted or unsubstituted hetero-aryl, and substituted or unsubstituted hetero-aryl in hetero-aromatic alcohols, preferably has 5 or 6 ring members and contains, as the hetero-atom or hetero-atoms up to two nitrogen, oxygen and/or sulphur atoms and is, for example, unsubstituted or monosubstituted or polysubstituted pyridyl, thienyl or furyl, possible substituents being lower alkyl, lower alkoxy and halogens, in particular, in each case, those mentioned below, such as 2-, 3- or 4-pyridyl, 6-methyl-2-pyridyl, 6-methoxy-2-pyridyl or 2- or 3-thienyl.

Lower alkyl contains, for example, up to 7 and in particlar up to 4 C atoms and can be straight-chain or branched and bonded in any desired position, such as methyl, ethyl, propyl or n-butyl or also isopropyl, sec.-butyl or isobutyl.

Lower alkoxy, and also lower alkoxy in lower alkoxy-carbonyl, contains, for example, up to 7 and in particular up to 4 C atoms and can be straight-chain or branched and bonded in any desired position, such as methoxy, ethoxy, propoxy, isopropoxy, butoxy or amyloxy.

Lower alkanoyl, and also lower alkanoyl in lower alkanoyloxy, contains, for example, up to 7 and in particular up to 4 C atoms and can be straight-chain or branched, such as acetyl, propionyl, butyryl or isobutyryl.

Halogen is, for example, halogen having an atomic number of up to and including 35, such as fluorine, chlorine or bromine.

Salts of compounds of the general formula (I), in which R, $R_1$ and/or $R_2$ is carboxyl, are salts with bases, in particular corresponding salts which can be used pharmaceutically, such as alkali metal salts or alkaline earth metal salts, for example sodium salts, potassium salts, magnesium salts or calcium salts, and also ammonium salts with ammonia or amines, such as lower alkylamines or hydroxy-lower alkyl-amines, for example trimethylamine, triethylamine or di- or tri-(2-hydroxyethyl)-amine.

The novel compounds show valuable pharmacological properties. In particular, they show anti-allergic actions, which can be demonstrated, for example, on rats in doses of about 1 to about 100 mg/kg on oral administration in the passive cutaneous anaphylaxis test (PCA reaction), which is carried out analogously to the method described by Goose and Blair, Immunology, Volume 16, page 749 (1969), passive cutaneous anaphylaxis being produced by the procedure described by Ovary, Progr. Allergy, Volume 5, page 459 (1958). They also effect inhibition of the immunologically induced release of hystamine, for example from the peritoneal cells of rats infested with Nippostrongylus brasiliensis, in vitro, (cf. Dukor et al., Intern. Arch. Allergy (1976), to be published). Furthermore, they are highly active in various bronchoconstrictions induced artificially, as can be shown, for example, in the dosage range of about 1 to about 3 mg/kg, administered intravenously, with the aid of the bronchoconstriction produced by IgE antibodies in rats and in the dosage range of from about 1 mg/kg, administered intraveneously, with the aid of the bronchoconstriction induced by IgG antibodies in guinea pigs. The compounds of the present invention are useful as inhibitors of allergic reactions, for example in the treatment and prophylaxis of allergic diseases, such as asthma, including both extrinsic and intrinsic asthma, or other allergic diseases, such as hayfever, conjunctivitis, urticaria and eczema.

The invention relates, in particular, to compounds of the general formula I in which R is carboxyl, carboxy esterified by an alcohol of aliphatic or aromatic character or carbamyl which is unsubstituted or substituted by at least one substituted or unsubstituted hydrocarbon radical of aliphatic character, or a hetero-analogue thereof, or by a substituted or unsubstituted aryl radical, Ph is 1,2-phenylene which contains the group R—CO—NR$_3$— and is otherwise unsubstituted or is substituted, X is a group —CO—CR$_1$=CR$_2$—, in which $R_1$ and $R_2$ independently of one another are hydrogen, lower alkanoyl, benzoyl, free carboxyl, carboxyl esterified or amidated as indicated above for R or a substituted or unsubstituted hydrocarbon radical of aliphatic character or an aromatic hydrocarbon radical, or a hetero-analogue thereof, or conjointly are 1,3-, 1,4- or 1,5-lower alkylene, and $R_2$ can also be free hydroxyl or hydroxyl etherified by a lower alkanol or esterified by a lower alkanecarboxylic acid, and $R_3$ is hydrogen or lower alkyl, possible substituents of aromatic and heteroaromatic groups being, in each case, in particular lower alkyl, such as methyl, lower alkoxy, such as methoxy, halogen, such as chlorine, hydroxyl and trifluoromethyl, in the free form or in the form of a salt.

The invention relates, in particular, to compounds of the general formula I in which R is carboxyl, carboxyl esterified by a lower alkanol which is unsubstituted or substituted by substituted or unsubstituted phenyl or carboxyl esterified by a substituted or unsubstituted phenol, or carbamyl which is unsubstituted, monosubstituted by lower alkyl, substituted or unsubstituted phenyl-lower alkyl or substituted or unsubstituted phenyl, for example a group

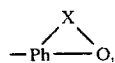

in which Ph and X are as defined below, or disubstituted by lower alkyl or by lower alkylene or a heteroanalogue thereof, Ph is 1,2-phenylene which contains the group R—CO—NR$_3$— and is otherwise unsubstituted or is substituted, X is a group —CO—CR$_1$=CR$_2$—, in which R$_1$ and R$_2$ independently of one another are hydrogen, lower alkanoyl, such as acetyl, free carboxyl or carboxyl esterified by a lower alkanol, such as methanol, lower alkyl which is unsubstituted or substituted by phenyl, which, in turn, can be substituted, or substituted or unsubstituted phenyl or 5-membered to 6-membered heteroaryl containing a nitrogen, oxygen or sulphur atom, or conjointly are tri-, tetra- or penta-methylene and R$_2$ can also be free hydroxyl or hydroxyl etherified by a lower alkanol, such as methanol, or esterified by a lower alkanecarboxylic acid, such as acetic acid, and R$_3$ is hydrogen or lower alkyl, possible substituents of phenyl, phenol, 1,2-phenylene Ph and heteroaryl being lower alkyl, such as methyl, lower alkoxy, such as methoxy, halogen, such as chlorine, hydroxyl and trifluoromethyl, in the free form or in the form of a salt.

The invention relates especially, on the one hand, to compounds of the general formula Ia

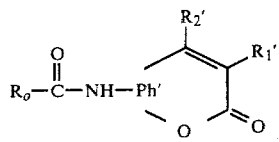

and, on the other hand, to compounds of the general formula Ib

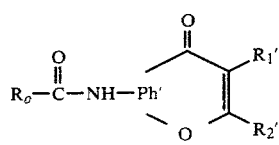

in which, in each case, R$_o$ is carboxyl, lower alkoxycarbonyl, such as methoxy- or ethoxy-carbonyl, phenyl-lower alkoxy-carbonyl which in the phenyl part is unsubstituted or substituted as indicated below, such as benzyloxycarbonyl, or free carbamyl, carbamyl monosubstituted or disubstituted by lower alkyl, such as methyl or ethyl, or carbamyl disubstituted by tetra- or penta-methylene or 3-oxa-, 3-aza- or 3-thia-pentametylene, Ph' is 1,2-phenylene which contains the group R$_o$—CO—NH— and, in addition, is otherwise unsubstituted or is substituted as indicated below, R$_1$' and R$_2$' conjointly are tri-, tetra- or penta-methylene, or R$_1$' is hydrogen, lower alkanoyl, such as acetyl, carboxyl, lower alkoxy-carbonyl, such as methoxy- or ethoxy-carbonyl, lower alkyl, such as methyl, or phenyl or pyridyl which are unsubstituted or substituted as indicated below, and R$_2$' has one of the meanings given for R$_1$' or is hydroxyl, lower alkoxy, such as methoxy, or lower alkanoyloxy, such as acetoxy, possible substituents of substituted phenyllower alkoxy-carbonyl R' or additionally substituted 1,2-phenylene Ph' and of substituted phenyl and pyridyl R$_1$' and/or R$_2$' being, lower alkyl, such as methyl, lower alkoxy, such as methoxy, halogen, such as chlorine, hydroxyl and trifluoromethyl, in each case in the free form or in the form of a salt.

The invention relates primarily on the one hand to compounds of the general formula Ia in which R$_o$ is carboxyl or lower alkoxy-carbonyl having up to 5 C atoms, such as methoxy- or ethoxy-carbonyl, Ph' is 1,2-phenylene which contains the group R$_o$—CO—NH, for example bonded in the 4-position or 5-position, and is otherwise unsubstituted or substituted in one of the free positions by lower alkyl or lower alkoxy having, in each case, up to 4 C atoms, such as methyl or methoxy, or hydroxyl or halogen, such as chlorine, R$_1$' is hydrogen or lower alkyl or lower alkanoyl, having, in each case, up to 4 C atoms, such as methyl or acetyl, or is phenyl or pyridyl and R$_2$' has one of the meanings given for R$_1$' or is hydroxyl or lower alkoxy having up to 4 C atoms, such as methoxy, and, on the other hand, to compounds of the general formula Ib in which R$_o$ and Ph' are as defined above and R$_1$' and R$_2$' independently of one another are hydrogen, lower alkyl having up to 4 C atoms, such as methyl, or phenyl, in each case in the free form or in the form of a salt.

The invention relates very particularly to compounds of the formula Ic

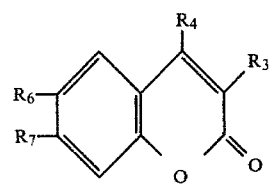

in which one of the radicals R$_6$ and R$_7$ is a group of the formula R$_o$'—CO—NH, in which R$_o$' is carboxyl or, less preferentially, lower alkoxy-carbonyl having up to 5 C atoms, such as methoxy- or ethoxy-carbonyl, and the other is hydrogen and R$_3$ and R$_4$ independently of one another are hydrogen or lower alkyl having up to 4 C atoms, such as methyl, in the free form or in the form of a salt.

The novel compounds can be prepared according to processes which are known per se.

A preferred procedure comprises, for example, the reaction of a compound of the general formula II

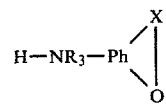

in which Ph, R₃ and X have the defined meanings, or a salt thereof, with a functionally modified oxalic acid of the formula R—Y in which Y is an esterified carboxyl group or a carboxyl group which has been converted to an anhydride with a hydrogenhalide acid and, if desired, the conversion of a compound thus obtained into another compound of the general formula (I) and/or the conversion of a resulting salt-forming compound into a salt or of a resulting salt into the free compound.

Salts of compounds of the formula II are, for example, hydrohalides, such as hydrochlorides, thereof and also salts with oxalic acid or monoester or monoamide thereof.

Functional derivatives of oxalic acid are for example symmetrical oxalic acid diesters, such as di-lower alkyl esters, and esterified halogenooxalic acids of the formula R-CO-Hal, in which Hal is chlorine or bromine.

The reaction can be carried out in a customary manner, especially in the manner known from the literature for analogous reactions, if necessary in the presence of a condensing agent, for example in the presence of a basic condensing agent, such as a tertiary organic nitrogen base, for example triethylamine or pyridine, or of an alkali metal hydroxide or alkali metal carbonate, for example of sodium hydroxide or potassium hydroxide, in the case of the reaction with an ester-halide of oxalic acid, and/or in an inert solvent, preferably an inert polar solvent, such as a N,N-dialkylamide, for example in N,N-dimethylformamide or N,N-dimethylacetamide.

With this reaction, oxalic acid ester-amides and/or symmetrical oxalic acid diamides of the general formula (I) can be obtained, in accordance with the particular molar ratios and concentration ratios of the oxalic acid component used and on the reaction conditions. If, for example, the equimolar amount of an oxalic acid ester-halide is added to a solution of the amine component of the general formula (II) and a tertiary organic nitrogen base at a moderate reaction temperature, for example at 0° to 80° and preferably 15° to 50°, or if the equimolar amount of an oxalic acid diester is initially introduced and the amine component is added, oxalic acid ester-amides of the general formula (I) are preferentially obtained. Conversely, when an excess of the amine component is used under more drastic reaction conditions and/or the amine component is initially introduced, symmetrical oxamides of the general formula (I) are preferentially obtained from the reaction with oxalic acid diesters.

The novel compounds can also be prepared by converting in a compound of the formula

a radical R' of the formula X₁—NR₃— in which X₁ denotes a halogenooxalyl group, into a group of the formula R—CO—NR₃— by solvolysis, or a radical R' of the formula X₂—NR₃— in which X₂ denotes a glyoxyloyl group or an optionally etherfied glycoloyl group, into an optionally esterified oxaloamino group R—CO—NR₃— by oxidation and, if desired, converting a compound which is thus obtainable into another compound of the formula I and/or converting a resulting salt into the free compound or into another salt or converting a resulting salt-forming compound into a salt.

In this context, halogenooxalyl X₁ is especially chlorooxalyl and solvolysis means hydrolysis, alcoholysis (reaction with the alcohol corresponding to the desired esterified carboxyl group R-) and/or ammono- or aminolysis (reaction with ammonia or an amine corresponding to the desired amidated carboxyl group).

Thus, for example, a halogenooxalyl group X₁ can be converted into the free oxalo group by hydrolysis, for example in the presence of an acid or basic agent, such as of a mineral acid, for example hydrochloric acid, or of an alkali metal hydroxide, for example sodium hydroxide solution or potassium hydroxide solution, the reaction preferably being carried out under acid conditions and/or in the presence of an oxidising agent, for example hydrogen peroxide, in the case of the hydrolysis of cyanocarbonyl groups or of thiooxalo groups of the oxalo group. The reaction is, if necessary, carried out in a polar solvent, such as a lower alkanol, ketone or ether, for example in ethanol, acetone or dioxane, and/or with cooling or warming, for example at about 0° C. to about 100° C.

A halogenooxalyl group X₁ can also be converted into esterified oxalo groups by conventional alcoholysis, i.e. by reaction with the corresponding alcohol. The reaction is advantageously carried out in the presence of a basic condensing agent, for example of pyridine or triethylamine. In an analogous manner, a halogenooxalyl group X₁ can be converted into an amidated oxalo group R—C(=O)— by ammonolysis or aminolysis, i.e. by reaction with ammonia or a corresponding primary or secondary amine, preferably in the presence of a basic condensing agent, for example of sodium hydroxide, pyridine or triethylamine.

A glyoxyloyl group X₂ which can be hydrated can advantageously be formed in situ in the course of the oxidation reaction, for example from the acyl group of an aliphatic or araliphatic carboxylic acid which can be α,β-unsaturated or α,β-dihydroxylated, a glycoloyl group, which can be esterified on the hydroxyl group, or the glycyl group, or can be set free from one of its functional derivatives, for example from one of its acetals or imines. Acyl groups of carboxylic acids which can be α,β-unsaturated or α,β-dihydroxylated are, for example, alkanoyl groups, such as lower alkanoyl, for example acetyl, acyl groups of α,β-unsaturated aliphatic monocarboxylic or dicarboxylic acids, for example acryloyl, crotonyl or the acyl group of free or functionally modified fumaric acid or maleic acid, acyl groups of α,β-unsaturated araliphatic carboxylic acids, for example substituted or unsubstituted cinnamoyl, or acyl groups of aliphatic α,β-dihydroxydicarboxylic acids, such as of tartaric acid, or monofunctional carboxy derivatives, such as esters or amides, thereof. Esterified glycoloyl groups are, for example, glycoloyl groups esterified on the hydroxyl group by a mineral acid, such as a hydrogen halide acid, for example by hydrochloric acid or hydrobromic acid, or by a carboxylic acid, for example by acetic acid or substituted or unsubstituted benzoic acid. Acetalised glyoxyloyl groups are, for example, glyoxyloyl groups acetalised by lower alkanols or a lower alkane-diol, such as dimethoxy-, diethoxy- or ethylenedioxy-acetyl. Imines of glyoxyloyl groups are, for example, substituted or unsubstituted N-benzylimines or N-(2-benzothiazolyl)-imines thereof or imines with 3,4-di-tert.-butyl-o-quinone.

The oxidation can be carried out in a customary manner by reaction with a suitable oxidising agent. Suitable oxidising agents are, especially, oxidising heavy metal compounds, such as silver compounds, for example silver nitrate or silver picolinate, oxy-acids of heavy metals, for example of manganese-IV, manganese-VII, chromium-VI and iron-VI, or of halogens, or their anhydrides or salts, such as chromic acid, chromium dioxide, potassium dichromate, potassium permanganate, manganese dioxide, potassium ferrate, sodium iodate, sodium periodate or lead tetraacetate. The reaction with these oxidising agents is effected in a customary manner, for example in an inert solvent, such as acetone, acetic acid, pyridine or water, or a mixture, preferably an aqueous mixture, of inert solvents, at normal temperature or, if necessary, with cooling or warming, for example at about 0° C. to about 100° C. The oxidation of free or etherified glycoloyl groups to free or esterified oxalo groups is, for example, advantageously carried out with potassium permanganate in aqueous pyridine or acetone at room temperature. Acetalised glyoxyloyl groups and imino-acetyl groups are preferably oxidised under acid conditions, for example with potassium dichromate in sulphuric acid. Acyl groups of $\alpha,\beta$-dihydroxylated aliphatic carboxylic acids, such as the acyl radical of tartaric acid, are advantageously oxidised with periodic acid, whilst potassium ferrate in an alkaline medium, for example at pH=10 to 13, for example 11.5, or organic silver salts, such as silver picolinate, are preferably used for the oxidation of the glycyl group. Groups of the formula R—CH=N— are preferably oxidised with an organic per-acid, for example with peracetic acid or m-chloroperbenzoic acid, in an inert solvent, for example methylene chloride, chloroform or benzene.

A compound of the general formula I which is obtainable according to the invention can be converted into another compound of the general formula I in a manner which is known per se.

Thus, for example, a free carboxyl group R can be esterified to an esterified carboxyl group R in a customary manner, for example by treatment with a diazo-lower alkane, which is unsubstituted or substituted by substituted or unsubstituted aryl or hetero-aryl, or a tri-lower alkyl-oxonium, tri-lower alkyl-carboxonium or di-lower alkyl-carbonium salt, such as hexachloroantimonate or hexafluorophosphate, or, in particular, by reaction with the corresponding alcohol or a reactive derivative, such as a carboxylic acid ester, phosphorous acid ester, sulphurous acid ester or carbonic acid ester, for example a lower alkane-carboxylic acid ester, a tri-lower alkyl phosphite, di-lower alkyl sulphite or the pyrocarbonate, or a mineral acid ester or sulphonic acid ester, for example the hydrochloric acid ester or hydrobromic acid ester or sulphuric acid ester, benzenesulphonic acid ester, toluenesulphonic acid ester or methanesulphonic acid ester, of the corresponding alcohol, or with an olefin derived therefrom.

The reaction with the corresponding alcohol itself can advantageously be carried out in the presence of an acid catalyst, such as a proton-acid, for example hydrochloric acid or hydrobromic acid, sulphuric acid, phosphoric acid, boric acid, benzenesulphonic acid and/or toluenesulphonic acid, or a Lewis acid, for example boron trifluoride-etherate, in an inert solvent, especially an excess of the alcohol employed, and, if necessary, in the presence of a water-binding agent and/or with removal of the water of reaction by distillation, for example as an azeotrope, and/or at elevated temperature.

The reaction with a reactive derivative of the corresponding alcohol can be carried out in a customary manner and, when starting from a carboxylic acid ester, phosphorous acid ester, sulphurous acid ester or carbonic acid ester, can be carried out, for example, in the presence of an acid catalyst, such as one of those mentioned above, in an inert solvent, such as an aromatic hydrocarbon, for example in benzene or toluene, or in an excess of the alcohol derivative employed or of the corresponding alcohol, the water of reaction being distilled off if necessary, for example as an azeotrope. Starting from a mineral acid ester or sulphonic acid ester, the acid to be esterified is advantageously employed in the form of a salt, for example the sodium or potassium salt, and the reaction is carried out, if necessary, in the presence of a basic condensing agent, such as an inorganic base, for example sodium hydroxide or sodium carbonate, potassium hydroxide or potassium carbonate or calcium hydroxide or calcium carbonate, or of a tertiary organic nitrogen base, for example triethylamine or pyridine, and/or in an inert solvent, such as one of the above tertiary nitrogen bases or a polar solvent, for example in dimethylformamide, and/or at elevated temperature.

The reaction with an olefin can be carried out, for example, in the presence of an acid catalyst, for example a Lewis acid, for example boron trifluoride, or a sulphonic acid, for example p-toluenesulphonic acid, or, in particular, of a basic catalyst, for example sodium hydroxide or potassium hydroxide, advantageously in an inert solvent, such as an ether, for example in diethyl ether or tetrahydrofurane.

A free carboxyl group R can, furthermore, be converted into an amidated carboxyl group R by reaction with ammonia or an amine containing at least one hydrogen atom, in the customary manner, with dehydration of the ammonium salt formed as an intermediate, for example by azeotropic distillation with benzene or toluene or by dry heating.

The conversions, described above, of free carboxyl groups R into esterified or amidated carboxyl groups R can, however, also be carried out by first converting a compound of the formula I, in which R is carboxyl, into a reactive derivative in a customary manner, for example into an acid halide by means of a halide or phosphorus or sulphur, for example by means of phosphorus trichloride or phosphorus tribromide, phosphorus pentachloride or thionyl chloride, or into a reactive ester, i.e. esters having electron-attracting structures, such as the esters with phenol, thiophenol, p-nitrophenol or cyanomethyl alcohol, or a reactive amide, for example the amide derived from imidazole or 3,5-dimethylpyrazole, by reaction with a corresponding alcohol or amine, and then reacting the resulting reactive derivative in a customary manner, for example as described below for the transesterification, trans-amidation and inter-conversion of esterified and amidated carboxyl groups R, with a corresponding alcohol, ammonia or the corresponding amine containing at least one hydrogen atom, to give the desired group R.

An esterified carboxyl group R can, in a customary manner, be converted to a free carboxyl group R, for example by hydrolysis in the presence of a catalyst, for example of a basic or acid agent, such as a strong base, for example sodium hydroxide or potassium hydroxide, or a mineral acid, for example hydrochloric acid, sulphuric acid or phosphoric acid, or to an amidated carboxyl group R, for example by reaction with ammonia or the corresponding amine containing at least one hydrogen atom.

An esterified carboxyl group R can also be transesterified to another esterified carboxyl group R in a customary manner, for example by reaction with a metal salt, such as the sodium or potassium salt, of a corresponding alcohol or with the alcohol itself, in the presence of a catalyst, for example of a strong base, for example sodium hydroxide or potassium hydroxide, or of a strong acid, such as a mineral acid, for example hydrochloric acid, sulphuric acid of phosphoric acid, or of an organic sulphonic acid, for example p-toluenesulphonic acid, or of a Lewis acid, for example boron trifluoride etherate.

An amidated carboxyl group R can be converted to the free carboxyl group R in a customary manner, for example by hydrolysis in the presence of a catalyst, for example of a strong base, such as an alkali metal hydroxide or alkali metal carbonate or an alkaline earth metal hydroxide or alkaline earth metal carbonate, for example sodium hydroxide or sodium carbonate or potassium hydroxide or potassium carbonate, or of a strong acid, such as a mineral acid, for example hydrochloric acid, sulphuric acid or phosphoric acid.

Futhermore, in a compound obtainable according to the invention, free, esterified or etherified hydroxyl groups $R_2$ can be converted into one another.

Thus, for example, a free hydroxyl group $R_2$ can be esterified to a hydroxyl group $R_1$ and/or $R_2$ esterified by a carboxylic acid, by reaction with a preferably functionally modified carboxylic acid, such as a lower alkanecarboxylic acid, for example acetic acid, or etherified to an etherified hydroxyl group, for example a lower alkoxy group, $R_1$ and/or $R_2$, by reaction with an etherifying agent, for example with a lower alkylating agent.

A functionally modified carboxylic acid is, for example, an anhydride, such as the symmetrical anhydrides thereof, or an anhydride with a hydrogen halide acid, such as hydrochloric acid or hydrobromic acid, a reactive ester, i.e. an ester having electron-attracting structures, for example the phenyl, (p-nitro)-phenyl, or cyanomethyl ester of a lower alkanecarboxylic acid, or a reactive amide, for example an N-lower alkanoylimidazole or a N-lower alkanoyl-3,5-dimethyl-pyrazole.

Etherifying agents are, for example, reactive esterified alcohols, such as alcohols esterified by a mineral acid, for example by hydriodic acid, hydrochloric acid or hydrobromic acid or sulphuric acid, or an organic sulphonic acid, for example by p-toluenesulphonic acid, p-bromobenzenesulphonic acid, benzenesulphonic acid, methanesulphonic acid, ethanesulphonic acid or ethenesulphonic acid, or fluorosulphonic acid, and also diazoalkanes. Etherifying agents which may be mentioned in particular are lower alkyl chlorides, lower alkyl iodides and lower alkyl bromides, for example methyl iodides, di-lower alkyl sulphates, for example dimethyl sulphate or diethyl sulphate, or methyl fluorosulphonate, lower alkyl sulphonates, such as lower alkyl, for example methyl, p-toluenesulphonate, p-bromobenzenesulphonate, methanesulphonate or ethanesulphonate, and also diazo-alkanes, for example diazomethane.

The reactions with acids, preferably functionally modified acids, and with etherifying agents, for example those singled out above, can be carried out in a customary manner, for example in an inert solvent, such as an ether, for example in tetrahydrofurane, in the case of the reaction with a diazoalkane or, when reactive esterified alcohols are used, for example in the presence of a basic condensing agent, such as of an inorganic base, for example sodium hydroxide or sodium carbonate, potassium hydroxide or potassium carbonate or calcium hydroxide or calcium carbonate, or of a tertiary or quaternary nitrogen base, for example pyridine, α-picoline, quinoline or triethylamine, or tetraethyl-ammonium hydroxide or benzyltriethyl-ammonium hydroxide, and/or of a solvent customary for the particular reaction, which solvent can also comprise an excess of the functional acid derivative used for the esterification, for example of a lower alkanoic acid anhydride or acid chloride, or the lower alkyl halide or lower alkyl sulphate use, for example, for the etherification, and/or a tertiary nitrogen base used as the basic condensing agent, for example triethylamine or pyridine, if necessary at elevated temperature. Methylation by means of acyl iodide in amyl alcohol/potassium carbonate at the boiling point and also acylation by means of a lower alkanoic acid anhydride at 50°–150° or by means of a lower alkanoyl chloride in pyridine or pyridine-triethylamine at temperatures between −20° and +100° C. are especially to be recommended.

Conversely, etherified or, in particular, esterified hydroxyl $R_2$ can also be converted into hydroxyl in a customary manner, for example in the presence of an acid agent, such as a hydrogen halide acid, for example hydriodic acid, in an inert solvent, for example in ethanol or acetic acid.

Furthermore, in a compound obtainable according to the invention, acyl $R_2$ and/or, in particular, $R_1$ can be replaced by hydrogen. Thus, a carboxyl group $R_2$ and/or, in particular, $R_1$ can be decarboxylated in a customary manner, for example by the action of heat, or the acyl group $R_1$ of a carboxylic acid can be split off in a customary manner, such as by the action of basic agents, such as alkalis, for example dilute sodium hydroxide solution or, in particular, sodium carbonate solution, preferably about 5% strength sodium carbonate solution.

Depending on the choice of the starting materials and procedures, the novel compounds can be in the form of one of the possible isomers or in the form of a mixture thereof, for example in the form of isomers in respect of the orientation of X, and also, depending on the number of asymmetrical carbon atoms, in the form of pure optical isomers, such as antipodes, or in the form of mixtures of isomers, such as racemates, mixtures of diasteromers or mixtures of racemates.

Resulting mixtures of isomers in respect of the orientation of X, mixtures of diasteromers and mixtures of racemates can be separated on the basis of the physical/chemical differences between the constituents into the pure isomers, diasteromers or racemates in a known manner, for example by chromatography and/or fractional crystallisation.

Resulting racemates can also be resolved into the optical antipodes by known methods, for example by recrystallisation from an optically active solvent, with the aid of nitro organisms or by reaction of an acid end product with an optically active base which forms salts with the racemic acid and separation of the salts obtained in this way, for example on the basis of their different solubilities, into the diasteromers, from which the antipodes can be set free by the action of suitable agents. Advantageously, the more active of the two antipodes is isolated.

Resulting free compounds of the formula I, for example those in which R, $R_1$ and/or $R_2$ is carboxyl, can be converted into salts in a manner which is known per se, inter alia by treatment with a base or with a suitable salt of a carboxylic acid, usually in the presence of a solvent or diluent.

Resulting salts can be converted into the free compounds in a manner which is known per se, for example by treatment with an acid reagent, such as a mineral acid.

The compounds, including their salts, can also be obtained in the form of their hydrates or can incorporate the solvent used for crystallisation.

Because of the close relationship between the novel compounds in the free form and in the form of their salts, the free compounds or their salts, in the preceding and following text, are, where appropriate, also to be understood to include the corresponding salts or free compounds, in respect of general sense and intended use.

The invention also relates to those embodiments of the process in which a compound obtainable as an intermediate at any stage of the process is used as the starting material and the missing steps are carried out, or a starting material is used in the form of a salt and/or racemate or antipode or, especially, is formed under the reaction conditions.

The starting materials are known or, if they are novel, can be prepared according to methods which are known per se.

Thus, the starting materials of the general formula (II) can be prepared, for example, when, in a compound of the formula

(IIa)

in which Ph and X have the defined meanings and R″ is nitro or an acylated amino group which differs from a group of the formula $RCONR_3-$, the nitro group R″ is converted by conventional reduction, for example catalytically or using a metal and an acid, for example using iron and hydrochloric acid, or sodium hyposulphite in aqueous ammonia, into primary amino, or an acylated amino group R″ is converted by conventional hydrolysis, preferably in the presence of an acid, such as a mineral acid, for example hydrochloric acid or sulphuric acid, or of an inorganic base, for example sodium hydroxide solution or potassium hydroxide solution, into an amino group $—NHR_3$. Primary amino which is first formed can easily be alkylated to $—NHR_3$, for example using a lower alkyl halide.

Starting materials of the general formula (II) can also be prepared when a compound of the general formula

(IIb)

is subjected to a condensation reaction with an ester of an acid of the formula $R_2COCHR_1COOH$, or a compound of the formula

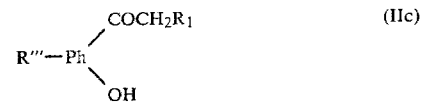
(IIc)

is subjected to a condensation reaction with an anhydride, for example with a carboxylic acid or hydrochloric acid, of an acid of the formula $R_2COOH$, R‴ in the formulae being hydrogen or a group $—NHR_3$ or R″, hydrogen R‴ is replaced by nitro by conventional nitration, nitro is reduced to amino and, if necessary, acylamino is hydrolysed to amino and/or amino is alkylated to $—NHR_3$. The reaction is carried out in a conventional manner, for example in the presence of a strongly acid condensing agent, such as a mineral acid, for example sulphuric acid, hydrochloric acid or hydrobromic acid, phosphoric acid or polyphosphoric acid, or of an aprotic acid condensing agent, such as an acid anhydride, for example phosphorus pentoxide or phosphorus oxychloride, or of a Lewis acid, for example aluminium trichloride, when starting from compounds IIb, or in the presence of a basic condensing agent, for example of an alkali metal carboxylate, such as sodium acetate in excess anhydride, or of potassium carbonate in acetone, when starting from compounds of the formula IIc. The compounds of the formula IIa, which have been mentioned above as starting materials, can also be prepared in an analogous manner.

Most of the compounds of the formula III which have been mentioned as starting materials are novel. In addition to the fact that they can be used as starting materials for the preparation of compounds of the formula I, some of them show further advantageous properties. Thus, compounds of the formula III in which R′ is a free or etherified glycoloylamino group, and also related compounds in which R′ is an esterified glycoloylamino group show the same pharmacological properties, in an activity of comparable strength, as the corresponding compounds of the formula I.

The invention accordingly also relates to novel starting materials, in particular compounds of the formula III in which R′ is a group of the formula $R_o—NR_3$ and $R_o$ is a free or etherified glycoloyl group or a glycoloyl group esterified by a carboxylic acid, processes for their preparation, pharmaceutical formulations containing these compounds and the use of these formulations as pharmaceuticals or for the preparation of medicaments.

Glycoloyl groups esterified by a carboxylic acid are to be understood as meaning, for example, glycoloyl groups esterified by an aliphatic or aromatic carboxylic acid, for example corresponding lower alkanoyloxyacetyl or substituted or unsubstituted benzoyloxyacetyl. Lower alkanoyloxyacetyl is, for example, acetoxy-, propionyloxy-, butyryloxy-, isobutyryloxy-, valeroyloxy-, caproyloxy- or pivaloyloxyacetyl. Possible substituents of substituted benzoyloxyacetyl groups are, in particular, lower alkyl, such as methyl, lower alkoxy, such as methoxy, and/or halogen, such as chlorine.

Etherified glycoloyl groups are, for example, glycoloyl groups etherified by a substituted or unsubstituted, aliphatic or araliphatic alcohol, such as corresponding lower alkoxy-acetyl or phenyl-lower alkoxy-acetyl groups. Substituents of lower alkoxy-acetyl are, in particular, hydroxyl, lower alkoxy and/or di-lower alkylamino and substituents of phenyl-lower alkoxy-acetyl groups are, for example, lower alkyl, such as methyl, lower alkoxy, such as methoxy, and/or halogen, such as chlorine. Lower alkoxy preferably has one of the meanings defined initially and phenyl-lower alkoxy-acetyl is especially benzyloxyacetyl or 2-phenylethoxyacetyl. Di-lower alkyl-amino-lower alkoxyacetyl is preferably 2-dimethyl- or 2-diethyl-aminoethoxyacetyl.

The invention relates especially to those compounds of the formula III in which Ph and $R_1$ have the meanings defined for the particular preferred catagories of the formula I, R' is a group $R_o$—$NR_3$ and $R_o$ is lower alkoxy-acetyl, in particular having up to 6 carbon atoms, such as methoxyacetyl or ethoxyacetyl, or, preferably, glycoloyl.

The compounds of the formula III, which have been mentioned as starting materials, can be prepared by methods which are known per se, preferably by reacting a compound of the formula

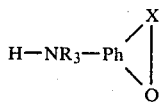 (II)

or an acid addition salt thereof, with a corresponding acid, for example of the formula $X_1$—OH (IIIa), $X_2$—OH (IIIb) or $R_o$—OH (IIIc), or a functional derivative thereof, and, if desired, converting a compound which is thus obtainable into another compound of the formula III in which R' is a group $R_o$—$NHR_3$.

Functional derivatives of acids of the formula IIIa to IIIc are, in particular, acid derivatives which contain an esterified or amidated carboxyl group or a carboxyl group in the form of an anhydride, such as lower alkoxy-carbonyl, substituted or unsubstituted carbamyl, for example carbamyl or imidazolyl-1-carbonyl, or halogenocarbonyl, for example chlorocarbonyl or bromocarbonyl. Examples which may be mentioned in particular of acids of the formula IIIa to IIIc and functional derivatives thereof are: oxalyl halides, such as oxalyl chloride or oxalyl bromide as functional derivatives of acids of the formula IIIa, as acids of the formulae IIIb and IIIc and functional derivatives thereof, glycollic acid and its lower alkyl esters and the corresponding lactide, or lower alkyl mono-lower alkoxy-acetates, such as ethyl mono-lower alkoxy-acetates, for example ethyl ethoxyacetate or ethyl diethoxyacetate, and for the preparation of precursors of compounds of the formula III in which R' is a group $X_2$—$NR_3$— and $X_2$ denotes glyoxyloyl, lower alkyl di-lower alkoxyacetates, halogenoacetic anhydrides, such as chloroacetic anhydride or chloroacetyl chloride and tartaric acid, or 2,3-diacetoxysuccinic anhydride, and also cinnamoyl chloride, acetyl chloride and glycine.

The reaction of compounds of the formula II with the above-mentioned acids and derivatives thereof can be carried out in a conventional manner, for example in the presence of a water-binding agent, such as an acid anhydride, for example phosphorous pentoxide, or dicyclohexylcarbodiimide, or of a condensing agent, for example an acid or basic condensing agent, such as a mineral acid, for example hydrochloric acid, or an alkali metal hydroxide or alkali metal carbonate, for example sodium hydroxide or potassium hydroxide, or of an organic nitrogen base, for example triethylamine or pyridine. In the case of the reaction with an acid anhydride, such as an acid chloride, an organic nitrogen base is preferably used as the condensing agent. The reaction with carboxylic acids is preferably carried out in the presence of a water-binding agent. If necessary, the reaction is in each case carried out in an inert solvent, at normal temperature or with cooling or warming, for example in the temperature range from about 0° C. to about 100° C., in a closed vessel and/or under an inert gas, for example nitrogen.

Compounds of the formula III in which R' is a group —$NHR_3$—$X_2$ and $X_2$ is glyoxyloyl can also be prepared when a corresponding halogeno acetyl compound, such as a bromoacetyl compound, is heated with hexamethylenetetramine, preferably in an aqueous alcohol, or is oxidised with silver tetrafluoborate in dimethylsulphoxide. Analogously, a chloroacetyl compound can also be oxidised with potassium dichromate in hexamethylphosphoric acid triamide in the presence of dicyclohexyl-18-crown-6-ether. Compounds of the formula III in which R' is a group $X_2$—$NHR_3$— and $X_2$ is an iminoacetyl group, for example substituted or unsubstituted benzyliminoacetyl, can be prepared starting from the corresponding glycyl compounds by reacting these with the corresponding carbonyl compound, for example with benzaldehyde, and rearranging the intermediate which is thus obtainable, for example a benzylideneglycyl compound, preferably under the reaction conditions. The compounds, according to the invention, of the formula III in which R' is a group of the formula $R_o$—$NHR_3$— and $R_o$ is a free or etherified glycoloyl group or a glycoloyl group esterified by a carboxylic acid can also be prepared by converting the radical R' in a compound of the formula III, in which R' is a radical which can be converted into the group $R_o NHR_3$—, into the desired group $R_o$—$NHR_3$— and, if desired, converting a compound which is thus obtainable into another compound of the formula III in which R' is a group $R_o NHR_3$—.

Radicals which can be converted into a group $R_o$—$NHR_3$— are those of the formula $X_1'$—$NHR_3$—, in which $X_1'$ is an esterified glycoloyl group which differs from a glycoloyl group which can be free or esterified by a carboxylic acid, for example a glycoloyl group esterified by a mineral acid, for example by a hydrogen halide acid, such as chloroacetyl or bromoacetyl. Groups $X_1'$ of this type can be converted to a glycoloyl group by hydrolysis, for example in the presence of a basic hydrolysing agent, such as sodium hydroxide solution, or into etherified glycoloyl groups or glycoloyl groups esterified by a carboxylic acid by reaction with a salt, such as an alkali metal salt, for example the sodium salt, of a corresponding alcohol or, respectively, of a corresponding carboxylic acid.

Further radicals R' which can be converted into groups of the formula $R_o$—$NHR_3$— are those of the formula $X_2'$—$NHR_3$—, in which $X_2'$ is a radical which can be converted by reduction into the glycoloyl group, such as the glyoxyloyl group, which can be in the form of a hydrate. This group can also be formed under the reduction conditions from an oxalo group, for example from an oxalo group in the free form or in the form of a salt, such as in the form of the sodium salt, or in the form of an anhydride or ester, such as halogenooxalyl, for example chlorooxalyl or bromooxalyl, or a mixed anhydride with diphenylphosphoric acid, or in the form of a lower alkyl ester, for example in the form of the methyl or isopropyl ester. The reduction of such groups is effected in a conventional manner. Starting from halogenooxalyl, catalytically activated hydrogen, for example hydrogen catalytically activated by palladium on a support, such as barium sulphate, if necessary in the presence of a sulphur-containing co-catalyst, such as thiourea, is preferably used. Anhydrides with diphenylphosphoric acid are advantageously reduced with an excess of sodium boronate. Oxalo groups in the form of a salt are advantageously reduced with a borane, such as diborane or a borane/ether complex, for example with borane in tetrahydrofurane, whilst oxalo groups in the form of an ester are advantageously reduced with sodium anilino-borohydride, which is obtainable by the reaction of sodium borohydride and acetanilide in pyridine.

A compound, according to the invention, of the formula III which is thus obtainable can be converted into another compound, according to the invention, of the formula III.

Thus, for example, the inter-conversions of free, esterified or etherified hydroxyl groups $R_2$ and the separation of isomers in respect of the orientation of X can be applied to the compounds according to the invention.

Furthermore, glycoloyl groups $R_o$ can be esterified by reaction with an esterifying agent, such as a corresponding carboxylic acid anhydride, for example a lower alkanoic acid anhydride or acid chloride, advantageously in the presence of a base, such as triethylamine or pyridine. Glycoloyl groups $R_o$ can also be etherified, for example by conversion into an alkali metal salt, such as the sodium salt, and reaction with a reactive derivative of the particular alcohol, such as a lower alkyl halide, for example a lower alkyl bromide, or a di-lower alkyl sulphate. Furthermore, glycoloyl groups $R_o$ esterified by a carboxylic acid can be hydrolysed to glycoloyl, for example in the presence of a hydrolysing agent, such as a base, such as sodium hydroxide solution.

In the process of the present invention, the starting materials used are preferably those which lead to the compounds described initially as being particularly valuable.

The present invention also relates to pharmaceutical formulations which contain one of the compounds, according to the invention, of the formula I or III or a salt thereof, which can be used pharmaceutically. The pharmaceutical formulations according to the invention are those which are intended for topical and local application and for enteral, such as oral or rectal, and parenteral administration to, and for inhalation by, warm-blooded animals and contain the pharmacological active compound on its own or together with an excipient which can be used pharmaceutically. The dosage of the active compound depends on the species of warm-blooded animal, the age and the state of health of the individual and also on the mode of administration.

The novel pharmaceutical formulations contain, for example, from about 10% to about 95%, and preferably from about 20% to about 90%, of the active compound. Pharmaceutical formulations according to the invention are, for example, those in the form of an aerosol or spray or in dosage unit forms, such as dragées, tablets, capsules or suppositories, and also ampoules.

The pharmaceutical formulations of the present invention are prepared in a manner which is known per se, for example by means of conventional mixing, granulating, dragée-making, dissolving or lyophilising processes. Thus, pharmaceutical formulations for oral use can be obtained by combining the active compound with solid excipients, granulating a resulting mixture if desired and processing the mixture or granules, after adding suitable auxiliaries if desired or necessary, to give tablets or dragée cores.

Suitable excipients are, especially, fillers, such as sugars, for example lactose, sucrose, mannitol or sorbitol, cellulose formulations and/or calcium phosphates, for example tricalcium phosphate or calcium hydrogen phosphate, as well as binders, such as starch pastes using, for example, maize starch, wheat starch, rice starch or potato starch, gelatine, tragacanth, methylcellulose and/or polyvinylpyrrolidone, and/or, if desired, disintegrating agents, such as the above-mentioned starches, and also carboxymethyl-starch, crosslinked polyvinylpyrrolidone, agar or alginic acid or a salt thereof, such as sodium alginate. Auxiliaries are, in particular, flow-regulating agents and lubricants, for example silica, talc, stearic acid or salts thereof, such as magnesium stearate or calcium stearate, and/or polyethylene glycol. Dragée cores are provided with suitable coatings, which, if desired, are resistant to gastric juices, and for this purpose, inter alia, concentrated sugar solutions, which can contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose formulations, such as acetylcellulose phthalate or hydroxypropylmethylcellulose phthalate, are used. Dyestuffs or pigments can be added to the tablets or dragée coatings, for example for identification or in order to characterize different doses of the active compound.

Other pharmaceutical formulations whch can be used orally are push-fit capsules made of gelatine, as well as soft, sealed capsules made of gelatine and a plasticiser, such as glycerol or sorbitol. The push-fit capsules can contain the active compound in the form of granules, for example mixed with fillers, such as lactose, binders, such as starches, and/or lubricants, such as talc or magnesium stearate, and can contain stabilisers. In soft capsules, the active compound is preferably dissolved or suspended in suitable liquids, such as fatty oils, liquid paraffin or liquid polyethylene glycols, it also being possible to add stabilisers.

Possible pharmaceutical formulations which can be used rectally are, for example, suppositories, which consist of a combination of the active compound with a suppository base. Suitable suppository bases are, for example, natural or synthetic triglycerides, paraffin hydrocarbons, polyethylene glycols or higher alkanols. In addition it is also possible to use gelatine rectal capsules which contain a combination of the active compound with a base; bases which can be used are, for example, liquid triglycerides, polyethylene glycols or paraffin hydrocarbons.

Formulations suitable for parenteral administration are, in particular, aqueous solutions of an active compound in the water-soluble form, for example of a water-soluble salt, and also suspensions of the active compound, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and can also contain stabilisers.

Inhalation formulations for the treatment of the respiratory passages by nasal or buccal administration are, for example, aerosols or sprays which can disperse the pharmacological active compound in the form of a powder or in the form of drops of a solution or suspension. Formulations which have powder-dispersing properties usually contain, in addition to the active compound, a liquid propellant gas which has a boiling point below room temperature and also, if desired, excipients, such as liquid or solid non-ionic or anionic surface-active agents and/or solid diluents. Formulations in which the pharmacological active compound is in solution contain, in addition to this active compound, a suitable propellant and also, if necessary, an additional solvent and/or a stabiliser. In place of the propellant gas, it is also possible to use compressed air and this can be produced as required by means of a suitable compression and pressure release device.

Pharmaceutical formulations for topical and local use are, for example, lotions and creams which contain a liquid or semi-solid oil-in-water or water-in-oil emulsion, and ointments (such formulations preferably containing a preservative) for the treatment of the skin, eyedrops which contain the active compound in aqueous or oil solution and eye ointments, which are preferably prepared in a sterile form, for the treatment of the eyes, powders, aerosols and sprays (similar to those described above for the treatment of the respiratory passages) and also coarse powders, which are administered through the nostrils by rapid inhalation, and nose-drops, which contain the active compound in aqueous or oily solution, for the treatment of the nose, or lozenges, which contain the active compound in a composition generally consisting of sugar and gum arabic or tragacanth, to which flavourings can be added, as well as pastilles, which contain the active compound in an inert composition, for example consisting of gelatine and glycerol or sugar and gum arabic, for the local treatment of the mouth.

The invention also relates to the use of the novel compounds of the formula (I) and salts thereof, as pharmacologically active compounds and especially as antiallergic agents, preferably in the form of pharmaceutical formulations. The daily dose which is administered to a warm-blooded animal weighing about 70 kg is from about 200 mg to about 1,200 mg.

The examples which follow illustrate the invention described above; however, they are not intended to restrict the scope of the invention in any way. Temperatures are given in degrees centrigrade.

EXAMPLE 1

35 g of 7-amino-4-methyl-coumarin and 24.5 g of triethylamine are initially introduced into 400 ml of dimethylformamide. A solution of 29.5 g of oxalic acid monomethyl ester-chloride in 100 ml of dimethylformamide is added dropwise to this mixture in the course of 15 minutes. The reaction temperature is kept below 35° by external cooling. The yellow, thick suspension is stirred overnight at room temperature and then poured into 2 liters of ice-water. The suspension is filtered with suction and the precipitate is recrystallised from acetone. This gives 7-methoxyoxalylamino-4-methyl-coumarin with a melting point of 248°–51°.

EXAMPLE 2

13.2 g of 7-amino-4,6-dimethyl-coumarin and 7 g of triethylamine are initially introduced into 250 ml of dimethylformamide and the mixture is warmed to 45°. Virtually everything goes into solution. 9.5 g of oxalic acid monomethyl ester-chloride in 100 ml of dimethylformamide are now added dropwise. The internal temperatue is kept below 45° by external cooling. Everything goes into solution at the start of the dropwise addition and a slight precipitate then separates out. The resulting suspension is stirred overnight at room temperature. The dimethylformamide is stripped off in vacuo and the residue is diluted with water and extracted by shaking with chloroform. The chloroform phase is separated off, washed with water, dried over anhydrous sodium sulphate and evaporated to dryness in vacuo. This gives crude 4,6-dimethyl-7-methoxyoxalyl-amino-coumarin which, after recrystallisation from chloroform, melts at 222°–5°.

EXAMPLE 3

3 g of 7-methoxyoxalylamino-4-methyl-coumarin are suspended in 50 ml of N sodium hydroxide solution and the suspension is stirred for 2½ hours at 30°–35°. A clear solution is obtained and this is acidified with dilute hydrochloric acid. The precipitate formed is filtered off with suction and recrystallized from acetone. This gives 2.6 g of 4-methyl-7-oxaloamino-coumarin with a melting point of 236°–38° (decomposition). The sodium salt melts above 300°.

EXAMPLE 4

The following compounds can also be prepared in a manner analogous to that described in Examples 1 to 3: 8-methoxyoxalylamino-4-methyl-coumarin, 7-methoxyoxalylamino-3-phenyl-coumarin, melting point 250°–252°, 7-methoxyoxalylamino-3-(3-pyridyl)-coumarin, 4-hydroxy-7-methoxyoxalylamino-coumarin, 6-methoxy-7-methoxyoxalylamino-coumarin, 6-methoxyoxalylamino-coumarin, 6-methoxyoxalylamino-4-methyl-coumarin, 3-acetyl-7-methoxyoxalylamino-coumarin, 3,4-dimethyl-7-methoxyoxalylamino-coumarin, melting point 258°–260°, 2,3-dimethyl-6-methoxyoxalylamino-chromone, 7-methoxyoxalylamino-3-methyl-flavone, 6-chloro-8-methoxyoxalylamino-4-methyl-coumarin, 4,6-dimethyl-8-methoxyoxalylamino-coumarin, 4,5-dimethyl-8-methoxyoxalylamino-coumarin, 3-acetyl-4-hydroxy-7-methoxyoxalyl-amino-coumarin, melting point 205°–206°, 6-methoxy-5-methoxyoxalyl-amino-coumarin and 4-methyl-7-(4-methyl-7-cumaryl)-aminooxalyl-amino-coumarin.

EXAMPLE 5

The following compounds can also be prepared in a manner analogous to that described in Examples 1 to 3: 7-ethoxyoxalylamino-4-methyl-coumarin, with a melting point of 218°–220°, starting from 8.7 g of 7-amino-4-methyl-coumarin and 3,4-dimethyl-7-oxaloamino-coumarin, with a melting point of 233°, starting from 5.5 g of 3,4-dimethyl-7-methoxyoxalylamino-coumarin.

EXAMPLE 6

10.5 g of 7-amino-4-methyl-coumarin are dissolved in 6 g of triethylamine and 70 ml of dimethylformamide and the solution is treated dropwise with 3.8 g of oxalyl chloride, with external cooling and while stirring. The mixture is stirred overnight at room temperature and poured into ice water, the resulting mixture is acidified to pH 5 to 6 with 2 N hydrochloric acid and the precipitate is filtered off with suction. The crystalline material is suspended in ethanol, the suspension is digested warm and the precipitate is filtered off with suction. This gives 4-methyl-7-(4-methyl-7-cumaryl)-aminooxalylamino-coumarin. This product is again digested with dimethylformamide and again filtered off with suction. It melts above 300°.

EXAMPLE 7

7-Methoxyoxalylamino-3-phenyl-coumarin with a melting point of 250°–252° can be prepared in a manner analogous to that described in Examples 1 and 2, starting from 6 g of 7-amino-3-phenyl-coumarin.

The starting material can be prepared as follows: 40 g of 2-methoxy-4-acetyl-amino-benzaldehyde and 223.2 g of benzyl cyanide are dissolved in 525 ml of ethanol, with warming. A mixture of 19.7 ml of 50% strength potassium hydroxide solution and 105 ml of ethanol is then added dropwise at 30°–35°. After stirring for 30 minutes at 40°–45°, the mixture is left to stand overnight. The reaction solution is then diluted with water, the ethanol is stripped off in vacuo and the aqueous phase is extracted thoroughly with ether. The dried ether solution is evaporated to dryness in vacuo and the residual oil is distilled under 0.1 mm Hg. α-Phenyl-2-methoxy-4-acetylamino-cinnamonitrile passes over at 62°. 63 g of α-phenyl-2-methoxy-4-acetylamino-cinnamonitrile are dissolved in 500 ml of warm toluene. A little nitrile precipitates again on cooling to 50°. 150 g of aluminium chloride are then added in 6 portions, and the internal temperature rises to 68°. The dark green mixture is kept at 80° for 6 hours. It is then poured on to a mixture of 800 g of ice and 100 ml of concentrated hydrochloric acid, the toluene is stripped off in vacuo and the product which has precipitated is filtered off with suction, 700 ml of 85% strength acetic acid and 120 ml of concentrated hydrochloric acid are poured over the product and the mixture is heated under reflux overnight. After cooling, crystalline 7-amino-3-phenyl-coumarin, which has separated out, is filtered off with suction and recrystallised from ethanol/ethyl acetate. It melts at 205°–208°.

EXAMPLE 8

N-Ethyl-7-methoxyoxalylamino-4-methyl-coumarin with a melting point of 136°–8° can be prepared in a manner analogous to that described in Examples 1 and 2, starting from 25.2 g of 7-ethylamino-4-methyl-coumarin.

7-Ethylamino-4-methyl-coumarin, which is used as the starting material, is obtained from 50 g of 3-ethylaminophenol by heating this with 55.5 g of ethyl acetoacetate and 39.7 g of zinc chloride in 190 ml of ethanol for 12 hours under reflux. For working up, the reaction mixture is poured into 3,000 ml of water, the resulting mixture is stirred for 2 hours and 7-ethylamino-4-methyl-coumarin is filtered off with suction. After recrystallisation from ethanol, it melts at 154°–155°.

EXAMPLE 9

N-Ethyl-7-oxaloamino-4-methyl-coumarin with a melting point of 142° is obtained in a manner analogous to that described in Example 3, starting from 14 g of N-ethyl-7-methoxyoxalylamino-4-methyl-coumarin.

EXAMPLE 10

N-Methyl-7-methoxyoxalylamino-4-methyl-coumarin with a melting point of 164°–165° is obtained in a manner analogous to that described in Examples 1 and 2, starting from 10.6 g of 7-methylamino-4-methyl-coumarin.

The starting material is prepared from 67.4 g of 3-methylamino-phenol in a manner analogous to that described in Example 7 for 7-ethyl-amino-4-methyl-coumarin. 7-Methylamino-4-methyl-coumarin melts at 193°–4°.

EXAMPLE 11

N-Methyl-7-oxaloamino-4-methyl-coumarin with a melting point of 162°–64° is obtained in a manner analogous to that described in Example 3, starting from 13.5 g of N-methyl-7-methoxyoxalylamino-4-methyl-coumarin.

EXAMPLE 12

8-Methoxyoxalylamino-7-methoxy-4-methyl-coumarin with a melting point of 228°–29° can be prepared in a manner analogous to that described in Examples 1 and 2, starting from 9.7 g of 8-amino-7-methoxy-4-methyl-coumarin.

The starting material can be prepared as follows:

A mixture of 16.3 ml of 65% strength nitric acid and 17 ml of concentrated sulphuric acid is added slowly dropwise to a solution of 45.5 g of β-methylumbelliferone in 100 ml of concentrated sulphuric acid with external cooling (internal temperature below 5°). After the dropwise addition has ended, the ice bath is removed and the mixture is stirred further at room temperature. As soon as the internal temperature has reached 20°, the mixture is poured into 1,200 ml of ice water and the product which has separated out is filtered off with suction. A mixture of 6-nitro- and 8-nitro-β-methylumbelliferone with a melting point of 223°–229° is obtained. This mixture is heated in acetone with 123.9 g of methyl iodide in the presence of 139.6 g of potassium carbonate for 19 hours under reflux. The acetone is stripped off in vacuo and the evaporated residue is treated with 400 ml of water. The material which has not dissolved is filtered off with suction. This gives 8-nitro-7-methoxy 4-methyl-coumarin with a melting point of 233°. 6-Nitro-β-methylumbelliferone with a melting point of 243° can be isolated, as the single product, from the filtrate by acidifying with concentrated acid.

8-Amino-7-methoxy-4-methyl-coumarin with a melting point of 152°–155° is obtained from 8-nitro-7-methoxy-4-methyl-coumarin by reducing the nitro group with sodium hyposulphite.

EXAMPLE 13

The following compounds can also be prepared in a manner analogous to that described in Examples 1 to 3: 8-oxaloamino-7-methoxy-4-methyl-coumarin starting from 8-methoxyoxalylamino-7-methoxy-4-methyl-coumarin, 6-methoxyoxalylamino-7-hydroxy-4-methyl-coumarin starting from 6-amino-β-methylumbelliferone (obtainable by reduction of the nitro group) and 6-oxaloamino-7-hydroxy-4-methyl-coumarin starting from 6-methoxyoxalylamino-7-hydroxy-4-methyl-coumarin.

EXAMPLE 14

4,6-Dimethyl-7-oxaloamino-coumarin, melting point 250°–251° (decomposition), 7-methoxyoxalylamino-3,4-tetramethylene-coumarin, melting point 231°–232°, and 7-oxaloamino-3,4-tetramethylene-coumarin monohydrate, melting point 235° (decomposition), can also be prepared in a manner analogous to that described in Examples 1 to 3.

EXAMPLE 15

2,3-Dimethyl-6-methoxyoxalylamino-4-oxo-4H-1-benzopyrane with a melting point of 242°–244° can be obtained in a manner analogous to that described in Examples 1 to 3, starting from 12 g of 2,3-dimethyl-6-amino-4-oxo-4H-1-benzopyrane.

The starting material can be prepared as follows:

150 g of phosphorus pentoxide are added to 100 g of ethyl 2-methylacetoacetate and 100 g of phenol in 300 ml of toluene, while stirring. After briefly warming to 40°, an exothermic reaction starts and the internal temperature rises up to 40°. The mixture is then warmed at an internal temperature of about 100° for 2 hours, cooled somewhat (about 80°) and, after adding a further 100 g of phenol and 100 g of phosphorus pentoxide, again heated at 100° for 2 hours. The reaction mixture is diluted with 300 ml of toluene and poured, while still hot, into 1,500 ml of ice-water. The resulting mixture is rendered alkaline with concentrated sodium hydroxide solution and saturated with sodium chloride. It is then stirred vigorously for 45 minutes and the organic phase is separated off, washed with 400 ml of 2 N sodium hydroxide solution and then with 600 ml of a saturated solution of sodium chloride, dried and evaporated to dryness. The residual oil is subjected to fractional distillation in vacuo and the fractions which pass over at 170°/13 mm are collected and crystallized from isopropanol/petroleum ether. The resulting 2,3-dimethyl-4-oxo-4H-1-benzopyrane with a melting point of 91°–3° is nitrated in 70 ml of concentrated sulphuric acid at below 5° with 6.9 ml of fuming nitric acid and 6-nitro-2,3-dimethyl-4-oxo-4H-1-benzopyrane, which is thus obtainable, is reduced, in dimethylformamide, with hydrogen in the presence of Raney nickel. 6-Amino-2,3-dimethyl-4-oxo-4H-1-benzopyrane, which is thus obtained, melts at 202°–204°.

EXAMPLE 16

7.4 g of 2,3-dimethyl-6-methoxyoxalylamino-4-oxo-4H-1-benzopyrane are warmed for 5 minutes at 70° with 26.9 ml of N sodium hydroxide solution in 100 ml of water. A solution forms. After stirring for 90 minutes at room temperature, the crystalline sodium salt of 2,3-dimethyl-6-oxaloamino-4-oxo-4H-1-benzopyrane, which has separated out and has a melting point about 265°, is filtered off.

EXAMPLE 17

7-Methoxyoxalylamino-2,3-dimethyl-4-oxo-4H-1-benzopyrane with a melting point of 228°–29° can be prepared in a manner analogous to that described in Example 1 and 2, starting from 17.2 g of 7-amino-2,3-dimethyl-4-oxo-4H-1-benzopyrane.

The starting material can be prepared as follows:

30 g of 2-hydroxy-4-acetylamino-propiophenone are heated with 14.3 g of anhydrous sodium acetate in 25.5 ml of acetic anhydride for 6 hours under reflux, the warm suspension is poured into ice-water, the resulting mixture is stirred for 30 minutes and the precipitate is filtered off with suction. 7-Acetylamino-2,3-dimethyl-4-oxo-4H-1-benzopyrane melts at 259°–61°. Saponification to give 7-amino-2,3-dimethyl-4-oxo-4H-1-benzopyrane (melting point 224°–26°) is effected by boiling under reflux in concentrated hydrochloric acid for 90 minutes.

EXAMPLE 18

7-Oxaloamino-2,3-dimethyl-4-oxo-4H-1-benzopyrane with a melting point of 234°–40° can be obtained in a manner analogous to that described in Example 3, starting from 9 g of 7-methoxyoxalylamino-2,3-dimethyl-4-oxo-4H-1-benzopyrane.

EXAMPLE 19

7-Methoxyoxalylamino-2-phenyl-3-methyl-4-oxo-4H-1-benzopyrane with a melting point of 239° is obtained in a manner analogous to that described in Example 1 and 2, starting from 11 g of 7-amino-2-phenyl-3-methyl-4-oxo-4H-1-benzopyrane.

The starting material can be prepared as follows:

35 g of 2-hydroxy-4-acetylaminopropiophenone, 23.8 g of benzoyl chloride and 169.1 g of potassium carbonate are heated in 3,800 ml of acetone for 8 hours under reflux. The acetone is stripped off in vacuo and the residue is treated with 1,200 ml of water. The resulting mixture is stirred well and the material which has not dissolved is filtered off with suction, washed successively with 5% strength sodium hydroxide solution and water and dried in vacuo. The resulting material is then heated with 420 ml of saturated methanolic hydrochloric acid for 1 hour under reflux. The methanol is distilled off in vacuo and the residue is treated with concentrated ammonia solution. The product which separates out is filtered off with suction and digested with toluene and 7-amino-2-phenyl-3-methyl-4-oxo-4H-1-benzopyrane with a melting point of 204°–206°, which remains undissolved, is filtered off.

7-Oxaloamino-2-phenyl-3-methyl-4-oxo-4H-1-benzopyrane with a melting point of 243° can be obtained in a manner analogous to that described in Example 3, starting from 7.5 g of 7-methoxyoxalylamino-2-phenyl-3-methyl-4-oxo-4H-1-benzopyrane.

EXAMPLE 20

1 g of 7-hydroxyacetamido-4-methyl-coumarin is dissolved in 60 ml of acetone and the solution is stirred with 1 g of potassium permanganate in 50 ml of water for 40 hours at room temperature. 7-Oxalo-amino-4-methylcoumarin is extracted with 2 N sodium hydroxide solution and precipitated by acidifying. It melts at 236°–238° with decomposition.

The starting material can be prepared as follows:

8.7 g of 7-amino-4-methyl-coumarin are stirred, under nitrogen, in a round-bottomed flask, together with 7.6 g of glycollic acid at an oil bath temperature of 150°–160°. The reaction mass becomes crystalline after about 30 minutes. It is diluted with water and the product is filtered off with suction and recrystallised from 200 ml of dimethylformamide and 100 ml of ethanol. 7-Hydroxyacetamido-4-methyl-coumarin with a melting point of 253°–254° is obtained.

EXAMPLE 21

The following compounds can also be prepared in a manner analogous to that described in Examples 1 to 20: 6-methoxyoxalylamino-4-oxo-4H-1-benzopyrane, 6-oxaloamino-4-oxo-4H-1-benzopyrane, 6-methoxyoxalylamino-2-methyl-4-oxo-4H-1-benzopyrane, 6-oxaloamino-2-methyl-4-oxo-4H-1-benzopyrane, 6-oxaloamino-3-(2-pyridyl)-coumarin, 8-methoxyoxalylamino-3-(2-pyridyl)-coumarin, 8-oxaloamino-3-(2-pyridyl)-coumarin, 6-methoxy-5-oxaloamino-coumarin, 8-methoxyoxalylamino-coumarin, 8-oxaloaminocoumarin, 5-methoxyoxalylamino-coumarin, 5-oxaloaminocoumarin-coumarin, 6-methoxy-5-methoxyoxalylamino-4-methyl-coumarin, 6-methoxy-4-methyl-5-oxaloamino-coumarin, 6-hydroxy-4-methyl-5-oxaloamino-coumarin, 6-hydroxy-4-methyl-5-oxaloamino-coumarin, 7-methoxy-4-methyl-8-oxaloamino-coumarin, melting point 214° and 7-methoxy-8-methoxyoxalylamino-4-methyl-coumarin, melting point 216°. 7-Methoxyoxalylaminocoumarin, 6-oxaloaminocoumarin, 7-oxaloaminocoumarin, 4-methyl-6-oxaloamino-coumarin, 4-hydroxy-6-methoxyoxalylaminocoumarin, 6-methoxyoxalylamino-3-(2-pyridyl)-coumarin, melting point 240°-242° (decomposition) and 4-hydroxy-6-oxaloaminocoumarin.

EXAMPLE 22

Tablets containing 0.1 g of 7-oxaloamino-4-methyl-coumarin are prepared as follows:

| Composition (for 1,000 tablets): | |
|---|---|
| 7-Oxaloamino-4-methyl-coumarin | 100 g |
| Lactose | 50 g |
| Wheat starch | 73 g |
| Colloidal silica | 13 g |
| Magnesium stearate | 2 g |
| Talc | 12 g |
| Water | q.s. |

The 7-oxaloamino-4-methyl-coumarin is mixed with a portion of the wheat starch and with the lactose and the colloidal silica and the mixture is forced through a sieve. A further portion of the wheat starch is mixed to a paste with five times the amount of water on a water bath and the above pulverulent mixture is kneaded with this paste until a slightly plastic mass has formed. The plastic mass is passed through a sieve of about 3 mm mesh width and dried and the dry granules are again forced through a sieve. The remainder of the wheat starch, the talc and the magnesium stearate are then mixed in and the resulting mixture is pressed to give tablets weighing 0.25 g (with a breaking groove).

Tablets containing, in each case, 100 mg of one of the compounds, of the general formula I, mentioned in Examples 1 and 2 can also be prepared in an analogous manner.

EXAMPLE 23

An approximately 2% strength aqueous solution, which is suitable for inhalation, of a water-soluble active compound according to the invention, in the free form or in the form of the sodium salt, can, for example, be prepared in the following composition:

| Composition | |
|---|---|
| Active compound, for example 4-methyl-7-oxaloamino-coumarin | 2,000 mg |
| Stabiliser, for example the disodium salt of ethylenediaminetetraacetic acid | 10 mg |
| Preservative, for example benzalkonium chloride | 10 mg |
| Freshly distilled water | to make up to 100 ml |

Preparation

The active compound is dissolved in freshly distilled water with the addition of the equimolecular amount of 2 N sodium hydroxide solution. The stabiliser and the preservative are then added. After all of the components have dissolved completely, the resulting solution is made up to 100 ml and filled into small bottles and these are sealed gas-tight.

2% strength inhalation solutions containing, as the active compound, a compound which is the object of the preparation in one of Examples 1, 2 and 4 can also be prepared in an analogous manner.

EXAMPLE 24

An approximately 2% strength aqueous solution, which is suitable for inhalation, of a water-soluble active compound according to the invention, in the free form or in the form of the sodium salt, can, for example, be prepared in the following composition:

| Composition | |
|---|---|
| Active compound, for example the sodium salt of 3,4-dimethyl-7-oxaloamino-coumarin | 2,000 mg |
| Stabiliser, for example the disodium salt of ethylenediaminetetraacetic acid | 10 mg |
| Preservative, for example benzalkonium chloride | 10 mg |
| Freshly distilled water | to make up to 100 ml |

Preparation

The active compound is dissolved in freshly distilled water. The stabiliser and the preservative are then added. After all of the components have dissolved completely, the resulting solution is made up to 100 ml and filled into small bottles and these are sealed gas-tight.

2% strength inhalation solutions containing, as the desired compound, another compound which is the object of the preparation in one of Examples 5 to 21 can also be prepared in an analogous manner.

EXAMPLE 25

Capsules suitable for insufflation and containing about 25 mg of an active compound according to the invention can, for example, be prepared in the following composition:

| Composition | |
|---|---|
| Active compound, for example 7-methoxyoxalyl-amino-4-methyl-coumarin | 25 g |
| Very finely ground lactose | 25 g |

Preparation

The active compound and the lactose are intimately mixed. The resulting powder is then sieved and filled in 50 mg portions into 1,000 gelatine capsules.

Insufflation capsules containing, in each case, a compound which is the object of the preparation according to one of Examples 2 to 4 can also be prepared in an analogous manner.

EXAMPLE 26

Capsules suitable for insufflation and containing about 25 mg of an active compound according to the invention can, for example, be prepared in the following composition:

| Composition |
|---|
| Active compound, for example 3,4-dimethyl-7- |

| Composition | |
|---|---|
| oxaloamino-coumarin | 25 g |
| Very finely ground lactose | 25 g |

Preparation

The active compound and the lactose are intimately mixed. The resulting powder is then sieved and filled in 50 mg portions into 1,000 gelatine capsules.

Insufflation capsules containing, in each case, another compound which is the object of the preparation according to one of Examples 5 to 19 can also be prepared in an analogous manner.

I claim:

1. A benzopyrane compound having the formula

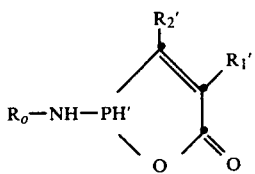

in which $R_o$ is glycoloyl or lower alkoxy-acetyl having up to 6 carbon atoms, Ph' is 1,2-phenylene which contains the group $R_o$—NH— and, in addition, is otherwise unsubstituted or is additionally substituted by lower alkyl, lower alkoxy, halogen, hydroxyl and trifluoromethyl, $R_1'$ and $R_2'$ conjointly are tri-, tetra- or pentamethylene, or $R_1'$ is hydrogen, lower alkanoyl, carboxyl, lower alkoxy-carbonyl, lower alkyl, or phenyl or pyridyl which are unsubstituted or substituted by lower alkyl, lower alkoxy, halogen, hydroxyl and trifluoromethyl, and $R_2'$ has one of the meanings given for $R_1'$ or is hydroxyl, lower alkoxy, or lower alkanoyloxy, or a pharmaceutically acceptable salt thereof.

2. A benzopyrane compound as claimed in claim 1, having the formula

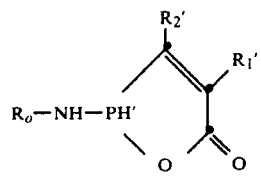

in which $R_o$ is glycoloyl or lower alkoxy-acetyl having up to 6 carbon atoms, Ph' is 1,2-phenylene which contains the group $R_o$—NH—, and is otherwise unsubstituted or substituted in one of the free positions by lower alkyl or lower alkoxy having, in each case, up to 4 C atoms, or hydroxyl or halogen, $R_1'$ is hydrogen or lower alkyl or lower alkanoyl, having, in each case, up to 4 C atoms, or is phenyl or pyridyl and $R_2'$ has one of the meanings given for $R_1'$ or is hydroxyl or lower alkoxy having up to 4 C atoms, or a pharmaceutically acceptable salt thereof.

3. A benzopyrane compound as claimed in claim 1, having the formula

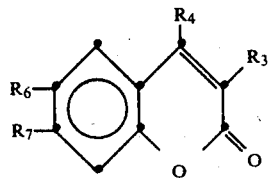

in which one of the radicals $R_6$ and $R_7$ is a group of the formula $R_o$—NH—, in which $R_o$ is glycoloyl, and the other is hydrogen and $R_3$ and $R_4$ independently of one another are hydrogen or lower alkyl having up to 4 C atoms, or a pharmaceutically acceptable salt thereof.

4. A compound as claimed in claim 1 and being 7-hydroxyacetamido-4-methyl-coumarin.

* * * * *